United States Patent [19]

Limburg et al.

[11] 4,232,103
[45] Nov. 4, 1980

[54] PHENYL BENZOTRIAZOLE STABILIZED PHOTOSENSITIVE DEVICE

[75] Inventors: William W. Limburg, Penfield; Damodar M. Pai, Fairport, both of N.Y.

[73] Assignee: Xerox Corporation, Stamford, Conn.

[21] Appl. No.: 69,649

[22] Filed: Aug. 27, 1979

[51] Int. Cl.³ .......................... G03G 5/04; G03G 5/14
[52] U.S. Cl. ........................................ 430/59; 430/58
[58] Field of Search ................................... 430/58, 59

[56] References Cited

U.S. PATENT DOCUMENTS

| | | | |
|---|---|---|---|
| 3,997,342 | 12/1976 | Bailey | 430/59 X |
| 4,053,311 | 10/1977 | Limburg et al. | 430/58 |
| 4,072,520 | 2/1978 | Rochlitz et al. | 430/59 |

FOREIGN PATENT DOCUMENTS 1337228  11/1973  United Kingdom .................... 430/58

Primary Examiner—Roland E. Martin, Jr.
Attorney, Agent, or Firm—James P. O'Sullivan; Harvey M. Brownrout; Peter H. Kondo

[57] ABSTRACT

An imaging member comprising a hole generation layer and a contiguous hole transport layer, said generation layer comprising a photoconductive material exhibiting the capability of photogeneration of holes and injection of said holes, said hole transport layer comprising a transparent electrically inactive polycarbonate resinous material having dispersed therein from about 25 to about 75% by weight of the composition of one or more of the following diamines:

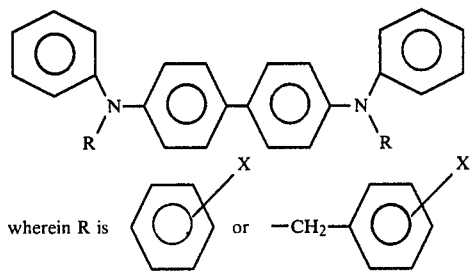

and wherein X is independently selected from the group consisting of an alkyl group having from 1 to about 4 carbon atoms and chlorine in the ortho, meta or para position, said transport layer also containing a chlorine-containing organic solvent, and a stabilizing proportion of a substituted or unsubstituted 2-(2'-hydroxyphenyl)-benzotriazole.

5 Claims, 1 Drawing Figure

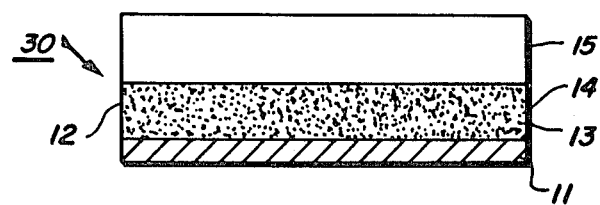

4,232,103

PHENYL BENZOTRIAZOLE STABILIZED PHOTOSENSITIVE DEVICE

BACKGROUND OF THE INVENTION

This invention relates in general to xerography and more specifically to a novel photosensitive device.

In recent years, interest has been shown in flexible electrophotographic plates for use in high speed office copying machines. Some of these plates are multilayered devices comprising, a conductive substrate layer, an adhesive-blocking interface layer, a charge generation layer and a charge transport layer. The charge transport layer comprises an organic charge transport molecule dissolved in a polymeric matrix material. This layer is substantially nonabsorbing in the spectral region of intended use, i.e. visible light, but is "active" in that it allows (1) injection of photogenerated holes from the charge generation layer and (2) efficient transport of these charges to the surface of the transport layer to discharge a surface charge thereon.

One class of hole transport molecules, N,N'-diphenyl-N,N'-bis(alkylphenyl)-[1,1'-biphenyl]-4,4'-diamines have been extensively studied as solutions or dispersions in polycarbonate polymers. The conductivity of this class of compounds in polycarbonate polymers has been found to increase under certain circumstances. As photoreceptor devices employing this class of compounds in the presence of a halogen-containing alkane solvent is subjected to ultraviolet radiation, a condition known as "cycle down" progressively develops as the device is cycled in the xerographic process. "Cycle down" refers to the progressive increase in conductivity of the transport layer and in a relatively short period of time the charge acceptance of the device deteriorates. Also, special precautions have to be taken with regard to the handling of the devices employing these compounds. They cannot be stored or left exposed to ambient room light for any length of time because fluorescent lamps employed in most buildings contain a UV component. This UV radiation causes devices left exposed to the room light to undergo gradual deterioration resulting in an increase in the conductivity of the transport layer.

OBJECTS OF THE INVENTION

It is therefore an object of this invention to provide a novel photosensitive device less susceptible to the deleterious effects of ultraviolet radiation degradation in the transport layer thereof.

It is a further object of this invention to provide an electrophotographic device free of "cycle down" problems caused by ultraviolet light induced increased conductivity.

PRIOR ART STATEMENT

Chemical stabilization of the physical properties of polymers has been well persued and a host of additives are available which stabilize various polymers against ultraviolet induced discoloration or ultraviolet induced mechanical failures. As far as is known, however, no study has been done to date on the chemical stabilization of electronic properties. By electronic stabilization is meant the elimination or minimizing of ultraviolet radiation induced traps or ultraviolet induced dark decay and the like. To be useful as an electronic stabilizer in a cyclic duplicating machine, the additive, in addition to preventing ultraviolet degradation, has to meet another strigent requirement. The additive should not introduce traps of its own under cyclic conditions, since even a small number of traps result in the cumulative trapping phenomenon generally referred to as "cycle up". The trap could be an isolated electronic state of the additive or it could result from the additive changing the character of the dispersion of the host molecule in the binder matrix. As indicated, no prior art appears to have dealt precisely with the problem outlined above.

SUMMARY OF THE INVENTION

The foregoing objects and others are accomplished in accordance with this invention by providing a photosensitive member comprising a generator layer and a transport layer wherein said transport layer comprises a solution or dispersion of a diamine of the class defined below and a residual amount of a halogen-containing organic solvent in a polycarbonate resin and a stabilizing proportion of a substituted or unsubstituted 2-(2'-hydroxyphenyl)-benzotriazole.

It has been found that the contribution of the transport layer to total dark decay of a virgin generator layer-transport layer photoreceptor of the present invention is small and, therefore, most of it originates in the generator layer. After exposure to long wavelength ultraviolet radiation, such as that contained in ambient room light, the transport layer contribution to the total dark decay can increase dramatically and surpass the generator layer contribution. When employing a diamine of the class defined below in a polycarbonate charge transport matrix, where the diamine is dissolved in the matrix via methylene chloride and more than a trace i.e. greater than 0.01% by weight, of methylene chloride based on the total weight of the transport layer, remains in the layer and the device is exposed to ambient light containing an ultraviolet light component, a significant deleterious increase in persistent conductivity quickly develops. This effect is not observed if the amount of methylene chloride amount is reduced to no more than a trace or if a non-chlorinated solvent is employed. It is, however, not practical to reduce the solvent to such a low level and non-halogenated solvents such as tetrahydrofuran are not good solvents for the high molecular weight polycarbonates. The solvent must be removed to less than about 3% by weight, in any event.

It has been found that when the halogenated solvent is present, the addition to the transport layer of a substituted or unsubstituted 2-(2'-hydroxyphenyl-benzotriazole significantly reduces or eliminates photoreactions leading to the deleterious effects of ultraviolet radiation which result in "cycle down". The use of this class of additives has no apparent deleterious effects of its own on the chemical or electrical properties of the hole transport layer.

In general, the advantages of the invention will become apparent upon consideration of the following disclosure of the invention, especially when taken in conjunction with the accompanying drawing wherein:

BRIEF DESCRIPTION OF THE DRAWING

The FIGURE is a schematic illustration of one of the members of the instant invention which comprise a photoreceptor having a charge generation layer overcoated with a charge transport layer.

DETAILED DESCRIPTION OF THE DRAWING AND INVENTION

Referring to the FIGURE, reference character 30 designates an imaging member which comprises a supporting substrate 11 having a charge generator layer 12 thereon. Substrate 11 is preferably comprised of any suitable conductive material. Typical conductors comprise aluminum, steel, nickel, brass or the like. The substrate may be rigid or flexible and of any convenient thickness. Typical substrates include flexible belts of sleeves, sheets, webs, plates, cylinders and drums. The substrate or support may also comprise a composite structure such as a thin conductive coating contained on a paper base; a plastic coated with a thin conductive layer such as aluminum, nickel or copper iodine; or glass coated with a thin conductive coating of chromium or tin oxide.

In addition, if desired, an electrically insulating substrate may be used. In this case, an electric charge, equivalent to a conductive layer, may be placed upon the insulating member by double corona charging techniques well known or disclosed in the art. Other modifications using an insulating substrate or no substrate at all include placing the imaging member on a conductive backing member or plate in charging the surface while in contact with said backing member. Subsequent to imaging, the imaging member may then be stripped from the conductive backing.

Generator layer 12 contains photoconductive particles dispersed randomly without orientation in binder 14.

Binder material 14 may comprise any electrically insulating resin such as those disclosed in Middleton et al U.S. Pat. No. 3,121,006, the entire contents of which are hereby incorporated by reference. Specific examples are polystyrene, acrylic and methacrylic ester polymers, polyvinylchlorides, etc. When using an electrically inactive or insulating resin, it is essential that there be particle to particle contact between the photoconductive particles. This necessitates that the photoconductive material be present in an amount of at least about 10% by volume of the binder layer with no limit on the maximum amount of photoconductor in the binder layer. If the matrix or binder comprises an active material, e.g., poly(N-vinyl carbazole), the photoconductive material need only comprise about 1% or less by volume of the binder layer with no limitation on the maximum amount of photoconductor in the binder layer. The thickness of binder layer 12 is not critical. Layer thicknesses from about 0.05 to 40.0 microns have been found to be satisfactory.

The photoconductive particles 13 may be any material capable of photogenerating holes and injecting photogenerated holes into the contiguous charge transport layer 15. Any suitable inorganic or organic photoconductor and mixtures thereof may be employed. Inorganic materials include inorganic crystalline photoconductive compounds and inorganic photoconductive glasses. Typical inorganic compounds include cadmium sulfoselenide, cadmium selenide, cadmium sulfide and mixtures thereof. Typical inorganic photoconductive glasses include amorphous selenium and selenium alloys such as selenium-tellurium, selenium-tellurium-arsenic and selenium-arsenic and mixtures thereof. Selenium may also be used in a crystalline form known as trigonal selenium.

Typical organic photoconductive materials which may be used as charge generators include phthalocyanine pigment such as the X-form of metal free phthalocyanine described in U.S. Pat. No. 3,357,989 to Byrne et al; metal phthalocyanines such as copper phthalocyanine; quinacridones available from duPont under the tradename Monastral Red, Monastral Violet and Monastral Red Y; substituted 2,4-diamino-triazines disclosed by Weinberger in U.S. Pat. No. 3,445,227; triphenodioxazines disclosed by Weinberger in U.S. Pat. No. 3,442,781; polynuclear aromatic quinones available from Allied Chemical Corporation under the tradename Indo Double Scarlet, Indofast Violet Lake B, Indofast Brilliant Scarlet and Indofast Orange. The photoconductive particles may be present in the generator layer in from 0.5% to about 95% by volume depending on the character of the binder material.

It is to be understood that the generator layer need not be dispersed photoconductive particles in a resin binder but can be a homogeneous layer, such as, amorphous selenium, selenium alloys e.g. selenium-tellurium-arsenic alloys and, in fact, any other charge generating photoconductive material which can withstand a minimum flexing stress required in a flexible photoreceptor.

Active layer 15 comprises a transparent electrically inactive polycarbonate resinous material having dispersed therein from about 25 to 75% by weight of the composition of one or more of the diamines within the scope of the following structural formula:

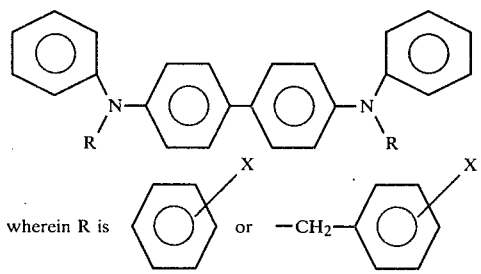

and wherein X is independently selected from the group consisting of an alkyl group having from 1 to about 4 carbon atoms (e.g. methyl, ethyl, propyl, butyl, etc.) and chlorine in the ortho, meta or para position.

In general, the thickness of active layer 15 would be from about 5 to 100 microns, but thicknesses outside this range can also be used.

The preferred polycarbonate resins for the transport layer have a molecular weight from about 20,000 to about 120,000, more preferably from about 50,000 to about 120,000.

Materials most preferred as the electrically inactive resinous material are poly(4,4'-isopropylidene-diphenylene carbonate) having molecular weights of from about 25,000 to about 40,000, available as Lexan ® 145, from about 40,000 to about 45,000, available as Lexan ® 141, both from the General Electric Company; and from about 50,000 to about 120,000 available as Makrolon ®, from Farbenfabricken Bayer AG; and from about 20,000 to about 50,000 available as Merlon ®, from Mobay Chemical Company.

Active layer 15, as described above, is substantially nonabsorbing to light in the wavelength region employed to generate holes in the photoconductive layer. This preferred range for xerographic utility is from about 4,000 to about 8,000 angstrom units. In addition, the photoconductor should be responsive to all wavelengths from 4,000 to 8,000 angstrom units if panchromatic responses are required. All photoconductor-active material combinations of the instant invention result in the injection and subsequent transport of holes across the physical interface between the photoconductor and the active material.

In order to effectively dissolve the charge transport diamine compound in the polycarbonate matrix, a suitable mutual solvent system must be employed. Methylene chloride i.e. $CH_2Cl_2$, is effective for this purpose, although other solvents such as chloroform and 1,2-dichloroethane can be employed. Non-halogen-containing organic solvents such as tetrahydrofuran are found to be poor solvents for the high molecular weight polycarbonate.

Dispersed or dissolved in the transport layer in order to greatly minimize or eliminate the deleterious effects of ultraviolet radiation is a stabilizing proportion of a substituted or unsubstituted 2-(2'-hydroxyphenyl)-benzotriazole having the following structural formula:

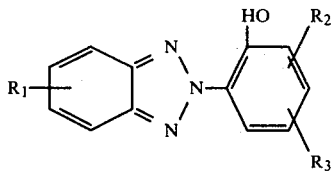

wherein $R_1$ is hydrogen or a $C_1$–$C_5$ alkyl, aryl, alkaryl, aralkyl, sulfhydryl, $NO_2$ or a halogen; and wherein $R_2$ and $R_3$ are independently selected from the group consisting of hydrogen $C_1$–$C_5$ alkyl, aryl, alkaryl, or aralkyl group.

Preferred compounds within this generic description are 2-(2'-hydroxy-3'-tert-butyl-5'-methylphenyl)-5-chlorobenzotriazole; 2-(2'-hydroxy-5'-methylphenyl)-benzotriazole and 2-(2'-hydroxy-3',5'-di-tert-butylphenyl)-benzotriazole.

These stabilizers usually are effective when present in an amount equal to from 0.1–10 weight % based on the weight of the transport compound. The following examples further specifically define the present invention with respect to the photosensitive member. The examples will show a comparison between charge transport layers not containing the stabilizing benzotriazole versus transport layers containing the stabilizing benzotriazole. The percentages are by weight unless otherwise indicated.

EXAMPLE I

A generator layer is prepared as follows: 2.4 grams of poly-N-vinylcarbazole is dissolved in 42 mls. of a 1:1 mixture of tetrahydrofuran and toluene. 2.4 grams of particulate trigonal selenium is added to the mixture which is then ball milled for about 72 hours in a 4 oz. bottle employing 300 grams of ⅛ inch diameter stainless steel shot. A 2 micron thick layer of this slurry is coated onto a substrate of aluminized Mylar which has been previously coated with a thin adhesive film, such as, DuPont 49000 ® polyester. This layer is heated at 100° C. for 18 hours in vacuum.

An approximately 25 micron thick transport layer is formed on top of the generator layer as follows: 1 gram of Makrolon ® polycarbonate and 1 gram of N,N'-diphenyl-N,N'-bis(3-methylphenyl)-[1,1'-biphenyl]-4,4'-diamine are dissolved in 10 mls of methylene chloride. A layer of 25 microns thick is overcoated onto the generator layer and heated at 80° C. in vacuum for four days to reduce the residual methylene chloride to a trace amount. The residual methylene chloride is less than about 0.01 weight % in the transport layer.

The xerographic testing of this device as well as the devices described in subsequent examples is carried out as follows: The layered device is negatively charged to a potential of about 1200 volts and the dark decay monitored for 5 seconds. The device is then exposed to a 2 microsecond flash of 4330 angstrom units wavelength and about 15 ergs/cm² intensity. The device of this Example is completely discharged by the light source, indicating that it is a xerographically operable device.

To examine the ultraviolet light stability of the device, it is exposed to an intense long wavelength UV source for 2 minutes, total photons $6 \times 10^{16}$/cm², and retested xerographically as above. The dark decay of the device is virtually the same as the rate of decay of the device before exposure to UV light. This shows that the performance of the device is substantially unaffected by ultraviolet light.

EXAMPLE II

This device is fabricated of the same materials and in the same manner as Example I except that the device is heated at 80° C. in vacuum for only 1 hour, instead of 72 hours, with the result that about 0.1 weight % methylene chloride remains in the transport layer. The device is xerographically tested before and after subjecting the device to the same exposed to ultraviolet light as in Example I. As a result of the UV exposure, the dark decay increased significantly.

EXAMPLE III

The device is fabricated as in Example II except that 7.5 weight % (based on the weight of the diamine) of 2-(2'-hydroxy-3'-tert-butyl-5'-methylphenyl)-5-chlorobenzotriazole was incorporated into the transport layer solution during the preparation of this layer. The device is xerographically tested before and after subjecting it to the same degree of UV radiation exposure. The dark decay is essentially unchanged as a result of exposure to the UV radiation. This establishes that the benzotriazole additive prevents UV induced increase in dark decay. It is also observed that the shape of the discharge curve when negatively charged and exposed to the light flash of 4300 angstrom units wavelength is essentially the same as that of Example I. This indicates that the additive does not deleteriously change the transport properties of the device.

EXAMPLE IV

A device is prepared as in Example II except that the solvent for the diamine and the polycarbonate is 10 ml of tetrahydrofuran. The polycarbonate is only partially soluble in the tetrahydrofuran and difficulty was experienced in filtering the undissolved fraction from this system. The undissolved fraction must be removed otherwise efficient charge transport is sacrificed. After removal and deposition of the transport layer on the generator layer, the device is heated at 80° C. for about 1 hour. This leaves a residual of about 0.1% by weight tetrahydrofuran in the transport layer.

The device is xerographically tested before and after the same degree of UV exposure as above. No increase in dark decay is observed as a result of the UV energy.

This indicates that no increase in dark decay or degradation of the device is caused by the presence of a residual of tetrahydrofuran and the influence of ultraviolet radiation.

EXAMPLE V p In preparing this device about 0.5 microns of amorphous selenium is vapor deposited on an aluminized Mylar substrate. The aluminum had a thin adhesive coating of DuPont 49000 ® polyester previously applied thereto.

A 25 micron thick transport layer of 1:1 by weight of the diamine and the polycarbonate is applied to the generator layer from a methylene chloride solution thereof. The device is heated at 40° C. for 18 hours. This leaves a considerable solvent residual of about 1.5% by weight. The device is tested xerographically before and after exposure to the same degree of UV energy as above. The dark decay increased enormously as a result of the UV expsoure.

EXAMPLE VI

The same device as in Example V was prepared except that 7.5 weight % (based on the weight of the diamine) of 2-(2'-hydroxy-3'-tert-butyl-5'-methylphenyl)-5-chlorobenzotriazole is incorporated into the transport layer. When tested xerographically before and after being subjected to the same UV exposure no increase in dark decay was observed. Further, the xerographic discharge characteristics were not changed by the presence of the additive.

EXAMPLE VII

This device was prepared incorporating only 1 weight % based on the weight of the diamine of benzotriazole in the transport layer. A significant inhibitory effect was observed in comparison to the device with no additive.

EXAMPLE VIII

A device similar to that of Example VI is prepared except that the transport molecule dissolved in the polycarbonate is N,N'-diphenyl-N,N'-bis(3-methylphenyl)-[1,1'-biphenyl]-4,4'-diamine and the additive is 7.5 weight % of 2-(2'-hydroxy-5'-methylphenyl)-benzotriazole. When xerographically tested before and after UV exposure as above, no increase in dark decay is observed.

EXAMPLE IX

A device similar to that of Example V is prepared except that the following diamine is employed as the charge transport molecule: N,N'-diphenyl-N,N'-bis(-phenylmethyl)-[1,1'-biphenyl]-4,4'-diamine. This diamine is incorporated into the polycarbonate as in Example V. The device is heated at reduced pressure at 40° C. for about 18 hours. This leaves a residual of about 1.5 by weight % methylene chloride in the transport layer. When tested xerographically before and after subjecting it to UV exposure as above a considerable increase in dark decay is observed.

EXAMPLE X

The device of Example IX is again prepared except the 7.5 weight % of 2-(2'-hydroxy-3'-tert-butyl-5'-methylphenyl)-5-chlorobenzotriazole is incorporated into the transport layer. After subjecting the device to UV exposure as above, no increase in dark decay is observed.

EXAMPLE XI

The same device as Example IX was prepared except that only 1 weight % of the benzotriazole was incorporated in the transport layer. A significant dark decay inhibitory effect was observed in comparison to the device with no additive.

What is claimed is:

1. In an imaging member comprising a hole generation layer and a contiguous hole transport layer, said generation layer comprising a photoconductive material exhibiting the capability of photogeneration of holes and injection of said holes, said hole transport layer comprising a transparent electrically inactive polycarbonate resinous material having dispersed therein from about 25 to about 75% by weight of the composition of one or more of the following diamines:

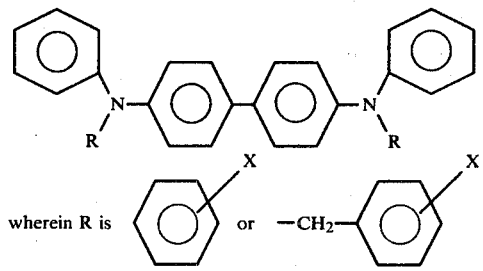

wherein R is and wherein X is independently selected from the group consisting of an alkyl group having from 1 to about 4 carbon atoms and chlorine in the ortho, meta or para position, said transport layer also containing a chlorine-containing organic solvent in an amount less than about 3% by weight of the transport layer, the improvement consisting of stabilizing said transport layer against the deleterious effects of ultraviolet light by the presence in said transport layer of a stabilizing proportion of a substituted or unsubstituted 2-(2'-hydroxyphenyl)-benzotriazole.

2. The member of claim 1 wherein the benzotriazole has the following general formula:

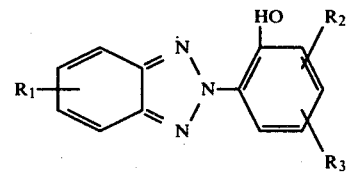

wherein $R_1$ is hydrogen or a $C_1$–$C_5$ alkyl, an aryl, alkaryl, aralkyl, sulfhydryl, $NO_2$ or a halogen; and $R_2$ and $R_3$ are independently selected from the group consisting of hydrogen, a $C_1$–$C_5$ alkyl, aryl, alkaryl or aralkyl group.

3. The member of claim 2 wherein said transport layer is stabilized by a member selected from the group consisting of 2-(2'-hydroxy-3'-tert-butyl-5'-methylphenyl)-5-chlorobenzotriazole; 2-(2'-hydroxy-5'-methylphenyl)-benzotriazole; and 2-(2'-hydroxy-3'-di-tert-butylphenyl)-benzotriazole.

4. The method of claim 3 wherein said photoconductive material is trigonal selenium and said diamine is N,N'-diphenyl-N,N'-bis(3-methylphenyl)-[1,1'-biphenyl]-4,4'-diamine.

5. The member of claim 3 wherein the benzotriazole compound is present in from about 0.1–10 percent by weight of the transport molecule.

* * * * *